(12) United States Patent
Takahashi et al.

(10) Patent No.: US 7,679,737 B2
(45) Date of Patent: Mar. 16, 2010

(54) METHOD, SYSTEM AND APPARATUS OF INSPECTION

(75) Inventors: Naohiro Takahashi, Kawasaki (JP); Kiyoshi Irino, Kawasaki (JP)

(73) Assignee: Fujitsu Microelectronics Limited, Yokohama (JP)

( * ) Notice: Subject to any disclaimer, the term of this patent is extended or adjusted under 35 U.S.C. 154(b) by 268 days.

(21) Appl. No.: 11/971,384

(22) Filed: Jan. 9, 2008

(65) Prior Publication Data

US 2008/0165352 A1 Jul. 10, 2008

(30) Foreign Application Priority Data

Jan. 10, 2007 (JP) .............. 2007-002430

(51) Int. Cl.
*G01N 21/00* (2006.01)

(52) U.S. Cl. .................. 356/237.4

(58) Field of Classification Search ........... None
See application file for complete search history.

(56) References Cited

U.S. PATENT DOCUMENTS 6,798,504 B2   9/2004  Sato et al.
6,809,809 B2 * 10/2004 Kinney et al. ............ 356/237.5
7,187,438 B2   3/2007  Hamamatsu et al.
2002/0154295 A1* 10/2002 Ivakhnenko et al. ..... 356/237.2

FOREIGN PATENT DOCUMENTS

| JP | 60010716 A | 1/1985 |
|----|------------|--------|
| JP | 2002098645 A | 4/2002 |
| JP | 2002257533 A | 9/2002 |

* cited by examiner

*Primary Examiner*—Tu T Nguyen
(74) *Attorney, Agent, or Firm*—Westerman, Hattori, Daniels & Adrian, LLP (57) ABSTRACT

A method of inspecting defects on an object includes irradiating predetermined particles with a laser beam to measure first scattered light intensities, irradiating plural types of defects with the laser beam to measure second scattered light intensities, determining types of some defects selected out of the plural types of defects using the first scattered light intensities, setting a discrimination line indicating a boundary value of the second scattered light intensities based on the determination, and discriminating, using the discrimination line, defects on the object.

18 Claims, 10 Drawing Sheets

METHOD, SYSTEM AND APPARATUS OF INSPECTION

CROSS-REFERENCE TO RELATED APPLICATIONS

This application is based upon and claims the benefits of priority from the prior Japanese Patent Application No. 2007-002430, filed on Jan. 10, 2007, the entire contents of which are incorporated herein by reference.

BACKGROUND

The present invention relates to an inspection method, an inspection system and an inspection apparatus. More particularly, the present invention relates to an inspection method, inspection system and inspection apparatus for inspecting an object to be inspected such as a wafer.

In manufacture of semiconductor devices, the presence or absence of defects on wafers in a manufacturing process, for example, peelings or flaws of a formed circuit pattern, scratches caused by polishing, and foreign particles such as etching residues is inspected to secure a high yield. When a defect is found in the inspection, causes of the defect are checked and measures for removing the causes are taken. In the thus performed inspection, if the defect cannot be highly accurately detected and a type of the detected defect cannot be appropriately determined, it is difficult to investigate the causes and accordingly, it is also difficult to take appropriate measures.

With relation to the wafer inspection, there has heretofore been used widely a method of inspecting the presence or absence of defects based on scattered light intensities and light receiving angles detected when irradiating a wafer surface with a laser beam. Further, there has also been proposed a method of respectively irradiating a specific part of a wafer with a laser beam from the directions approximately perpendicular to and oblique to its surface and comparing detected scattered light intensities with a predetermined reference value (discrimination line) to thereby discriminate between concave defects such as scratches or Crystal Originated Particles (COPs) and convex defects such as foreign particles adhered to a wafer surface see for example U.S. Pat. No. 6,798,504 and U.S. Pat. No. 7,187,438.

On a so-called CZ wafer currently used widely in manufacture of semiconductor devices, COPs are easily formed due to surface properties of the CZ wafer. Accordingly, in a case of using a wafer containing COPs in manufacture of semiconductor devices, the wafer inspection must be performed as follows. During the defect inspection, the COPs due to the wafer are accurately discriminated from defects such as foreign particles caused by some external factors in the manufacturing process, and the presence of COPs (the number of COPs and their positions) is grasped. At the same time, causes of the defects such as foreign particles discriminated from COPs are investigated and the investigation results are used for subsequent measures.

The method of discriminating between foreign particles and COPs includes a method of comparing scattered light intensities detected by laser beam irradiation at a predetermined angle with a predetermined discrimination line to thereby discriminate between foreign particles and COPs as described above. However, since the discrimination line is a line set by previously disposing standard particles each having a known particle size on a wafer and detecting scattered light intensities by laser beam irradiation at a predetermined angle to define a boundary between standard particles and COPs, the following problem occurs. When such a discrimination line is applied to the inspection of wafers having foreign particles generated in the manufacturing process, the defects may be regarded as COPs particularly near the discrimination line even though being actually foreign particles.

Further, in using a polished wafer, when similarly setting the discrimination line using standard particles in order to discriminate between foreign particles and scratches, there may arise the same problem as that in discriminating between foreign particles and COPs.

SUMMARY

A method of inspecting defects on an object includes irradiating predetermined particles with a laser beam to measure first scattered light intensities, irradiating plural types of defects with the laser beam to measure second scattered light intensities, determining types of some defects selected out of the plural types of defects using the first scattered light intensities, setting a discrimination line indicating a boundary value of the second scattered light intensities based on the determination, and discriminating, using the discrimination line, defects on the object.

DESCRIPTION OF THE PREFERRED EMBODIMENTS

By taking as an example a case of discriminating defects detected on wafers into foreign particles and COPs, preferred embodiments of the present invention will be described in detail below with reference to the accompanying drawings, wherein like reference numerals refer to like elements throughout.

First, principles of inspection will be described.

Figure 2:
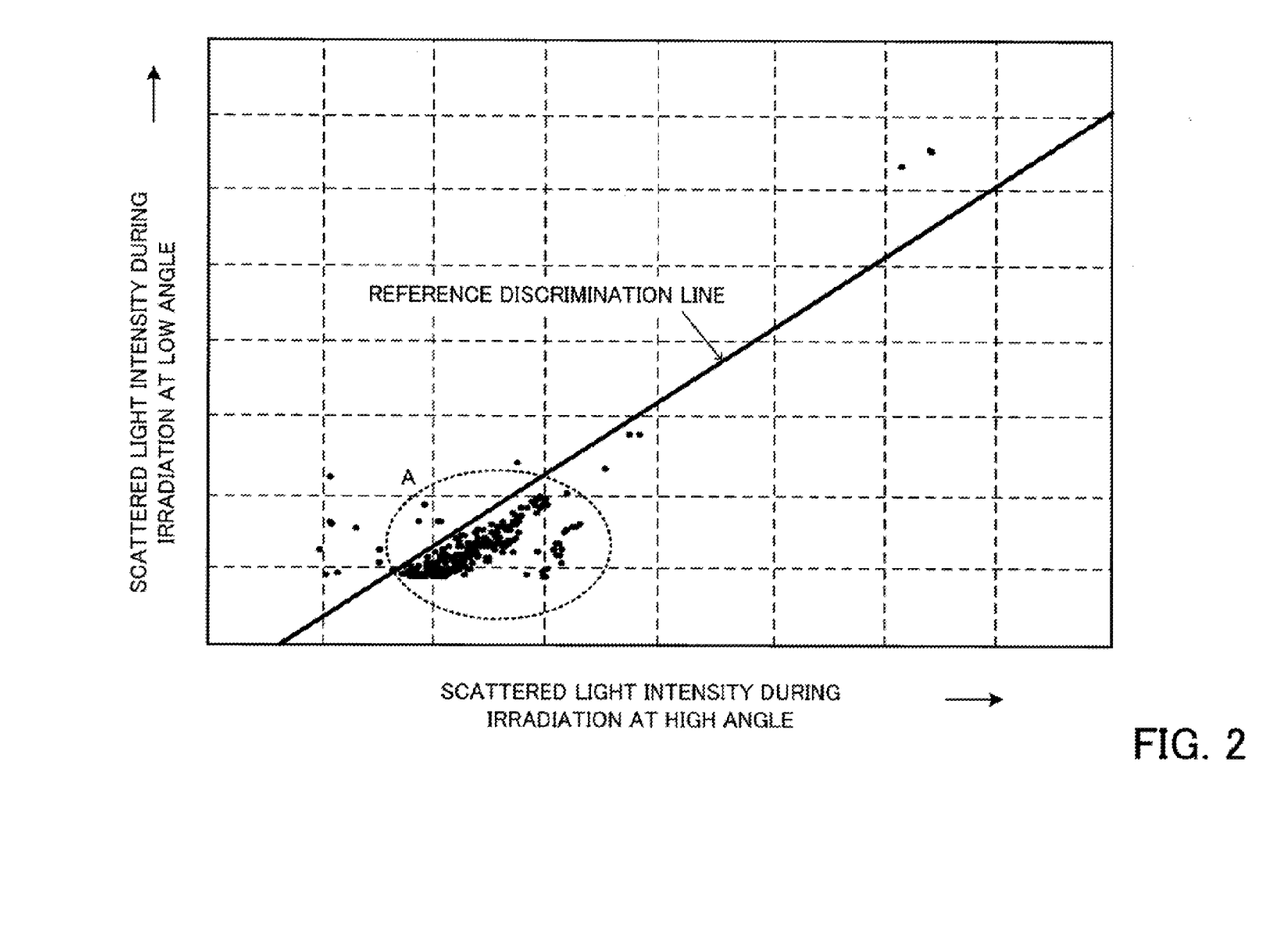
FIG. 2 shows one example of results of a laser scattering measurement.

FIG. 2 shows one example of results of a laser scattering measurement.

Defects on the wafer (defects here mean foreign particles and COPs) can be detected by the laser scattering measurement. In discriminating the defects on the wafer detected by the laser scattering measurement into foreign particles and COPs, there is used a discrimination line for discriminating the defects based on scattered light intensities obtained when irradiating the defects with a laser beam.

In foreign particles as convex defects, the scattered light intensity obtained when irradiating the particles with a laser beam at a low angle to the wafer surface and that obtained when irradiating the particles with a laser beam at a high angle (including a right angle to the wafer surface) to the wafer surface do not significantly change due to shapes of the foreign particles. Meanwhile, in COPs as concave defects, the scattered light intensity obtained when irradiating the COPs with a laser beam at a low angle to the wafer surface is reduced due to shapes of the COPs, as compared with that obtained when irradiating the COPs with a laser beam at a high angle.

Using such a property, defects on wafers are inspected as follows. First, the laser scattering measurement is performed by respectively irradiating with a laser beam at a low angle and at a high angle a wafer (a standard particle-adhering wafer) where plural types of standard particles each having a known particle size are adhered so as to be regarded as convex defects. Next, the obtained scattered light intensities are plotted by taking the scattered light intensity during irradiation at a high angle along the abscissa and by taking the scattered light intensity during irradiation at a low angle along the ordinate. Further, using the plotted data, a reference discrimination line as shown in FIG. 2 is set on a boundary between a data region of standard particles and a data region of the defects other than the standard particles.

The reference discrimination line can be normally represented by a linear function as shown in FIG. 2. In this case, the inclination represents a ratio between the scattered light intensities during irradiation at a low angle and at a high angle of laser beam (the scattered light intensity during irradiation at a low angle/the scattered light intensity during irradiation at a high angle). Meanwhile, the intercept represents the offset of the scattered light intensity during irradiation at a low angle of laser beam.

In FIG. 2, a region above the reference discrimination line is a data region of standard particles on the standard particle-adhering wafer, namely, of convex defects. Further, a region below the reference discrimination line is a data region of the defects other than the standard particles on the standard particle-adhering wafer, namely, of concave defects.

Similarly, the laser scattering measurement is performed by respectively irradiating with a laser beam at a low angle and at a high angle a wafer (foreign particle-adhering wafer) where foreign particles actually generated in the manufacturing process are attached as convex defects. Subsequently, the obtained scattered light intensities are plotted as shown in FIG. 2. Respective plotted points shown in FIG. 2 represent the scattered light intensities measured from the defects (foreign particles and COPs) on the foreign particle-adhering wafer.

When the defects on the foreign particle-adhering wafer are discriminated into foreign particles and COPs using only the reference discrimination line previously set using standard particles, foreign particles may be actually contained in the defects showing the scattered light intensities in the region below the reference discrimination line. That is, it is not necessarily appropriate to determine that on the assumption that the region above the reference discrimination line is a data region of convex defects and the region below the reference discrimination line is a data region of concave defects, the defects showing the scattered light intensities in the region above the reference discrimination line are foreign particles and the defects showing the scattered light intensities in the region below the reference discrimination line are COPs.

Therefore, in order to accurately discriminate the defects detected on the foreign particle-adhering wafer into foreign particles and COPs, the following method has been employed. That is, all the detected defects or great many defects selected out of all the detected defects, which show the scattered light intensities near the reference discrimination line, are evaluated by SEM to determine whether each defect is a foreign particle or a COP. Alternatively, the following method has been employed. That is, the scattered light intensity of the detected defect is corrected under predetermined conditions. Then, the corrected scattered light intensity is compared with the reference discrimination line to discriminate the defect into foreign particles and COPs based on whether the scattered light intensity is in the region above or below the reference discrimination line.

Here, the reference discrimination line is set using the standard particle-adhering wafer. Further, the approximation line of the scattered light intensities measured from the foreign particles is set using the foreign particle-adhering wafer. Subsequently, the discrimination line for discriminating the defects into foreign particles and COPs is set using the reference discrimination line and the approximation line.

Figure 1:
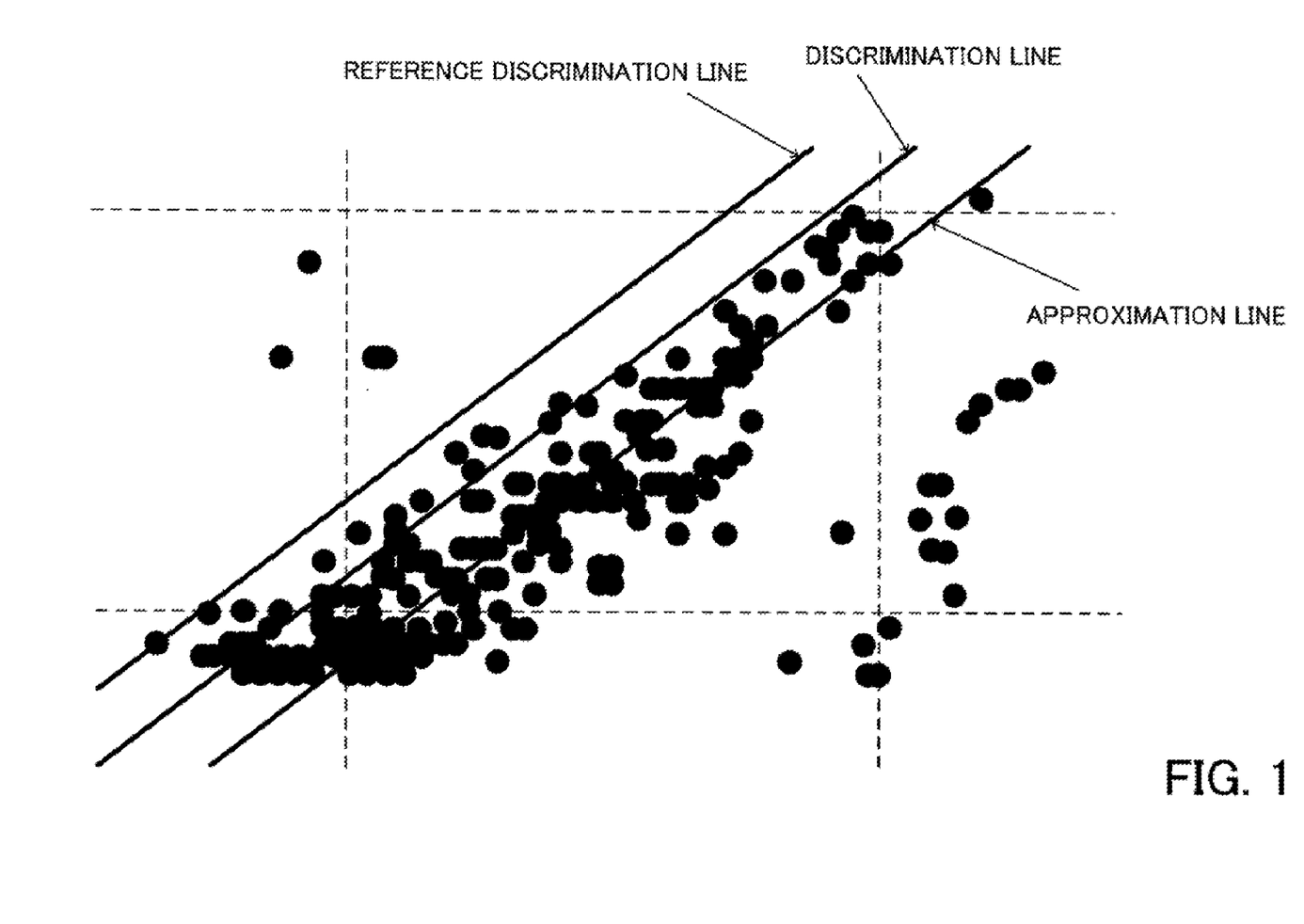
FIG. 1 illustrates set principles of a discrimination line.

FIG. 1 illustrates set principles of the discrimination line. FIG. 1 corresponds to an "A" portion of FIG. 2.

First, the reference discrimination line as shown in FIG. 1 is set using the standard particle-adhering wafer as described above. Then, the laser scattering measurement on the foreign particle-adhering wafer is performed. Subsequently, the scattered light intensities obtained from the defects (foreign particles and COPs) on the wafer are plotted to set the approximation line. The approximation line can be represented by a multidimensional function as well as represented by a linear function similarly to the reference discrimination line as shown in FIG. 1.

Further, some defects showing the scattered light intensities in the region between the reference discrimination line and the approximation line are selected out of the defects on the foreign particle-adhering wafer, from which the scattered light intensities are measured. Then, the some selected defects are evaluated by SEM to determine whether each defect is a foreign particle or a COP.

Next, based on the determination results, the scattered light intensities in the region between the reference discrimination line and the approximation line are discriminated into the scattered light intensities of foreign particles and those of COPs to thereby set the discrimination line as shown in FIG. 1 on a boundary between the foreign particles and the COPs. A region above this discrimination line is a data region of foreign particles and a region below this discrimination line is a data region of COPs.

When thus setting the discrimination line, defects detected on another wafer, for example, defects detected on a product wafer can be easily and accurately discriminated into foreign particles and COPs.

Figure 3:
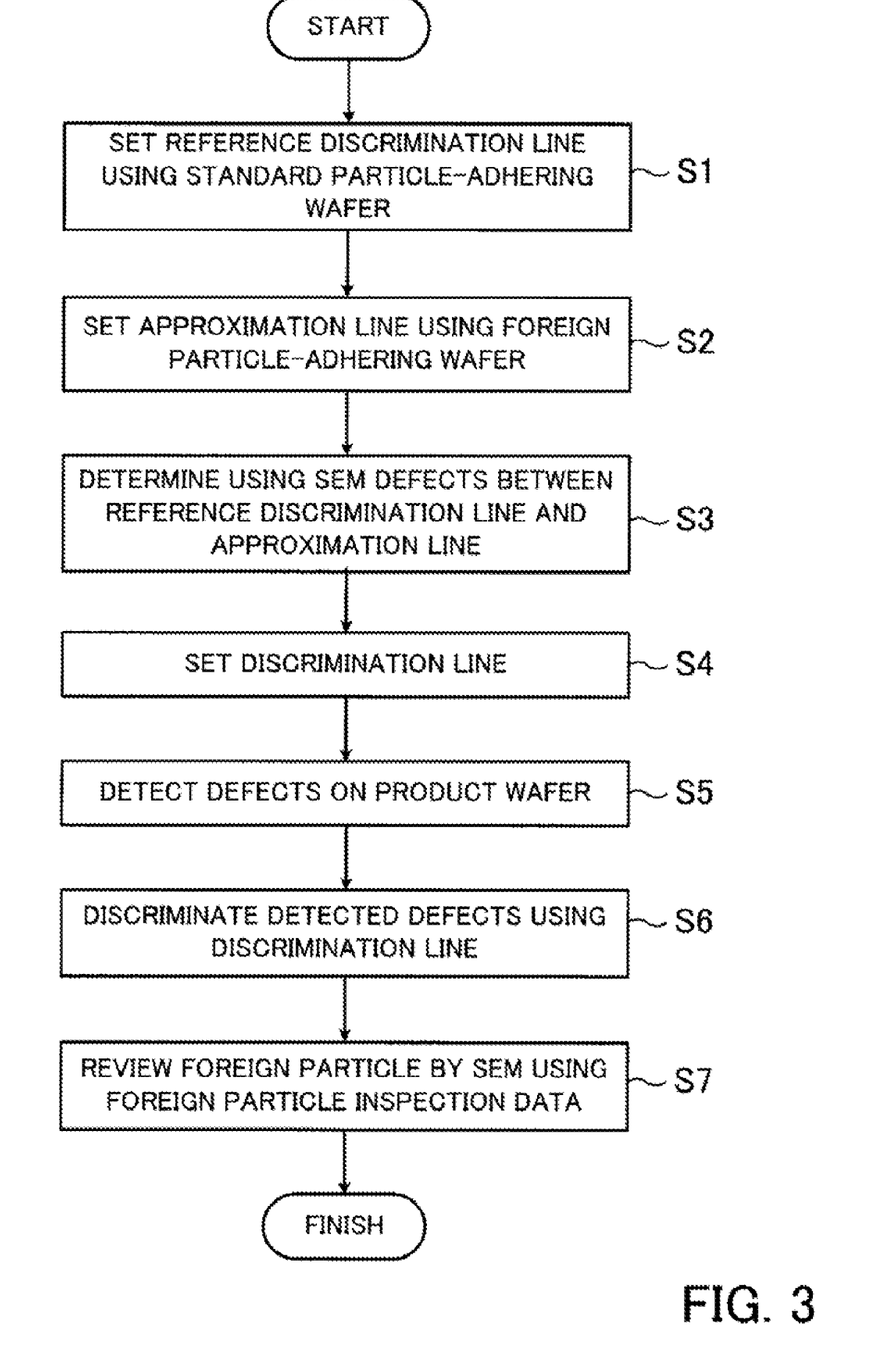
FIG. 3 shows one example of an inspection flow using a discrimination line.

FIG. 3 shows one example of an inspection flow using the discrimination line.

When performing inspection of a product wafer using the discrimination line, the inspection can be performed in the following flow.

Before the inspection of a product wafer, the discrimination line is set. When setting the discrimination line, the reference discrimination line is first set using the standard particle-adhering wafer as described above (step S1). Then, the laser scattering measurement is performed by irradiating with a laser beam at a low angle and at a high angle the foreign particle-adhering wafer to detect the defects (foreign particles and COPs) on the wafer. Then, the scattered light intensities obtained from the defects are plotted to set the approximation line (step S2). Next, some defects showing the scattered light intensities in the region between the reference discrimination line and the approximation line are selected out of the defects detected on the foreign particle-adhering wafer. Then, the some selected defects are evaluated by SEM to determine whether each defect is a foreign particle or a COP (step S3).

Further, based on the determination results, the scattered light intensities between the reference discrimination line and the approximation line are discriminated into the scattered light intensities of foreign particles and those of COPs, thereby setting the discrimination line on a boundary between the foreign particles and the COPS (step S4).

After the setting of the discrimination line, inspection of the product wafer is performed as follows. In the same manner as in the standard particle-adhering wafer and in the foreign particle-adhering wafer, the laser scattering measurement is first performed by irradiating with a laser beam at a low angle and at a high angle the product wafer to detect the defects on the product wafer (step S5). Then, the scattered light intensities of the detected defects are compared with the discrimination line set in Step S4 to thereby discriminate whether each defect is a foreign particle or a COP (step S6).

Figure 4:
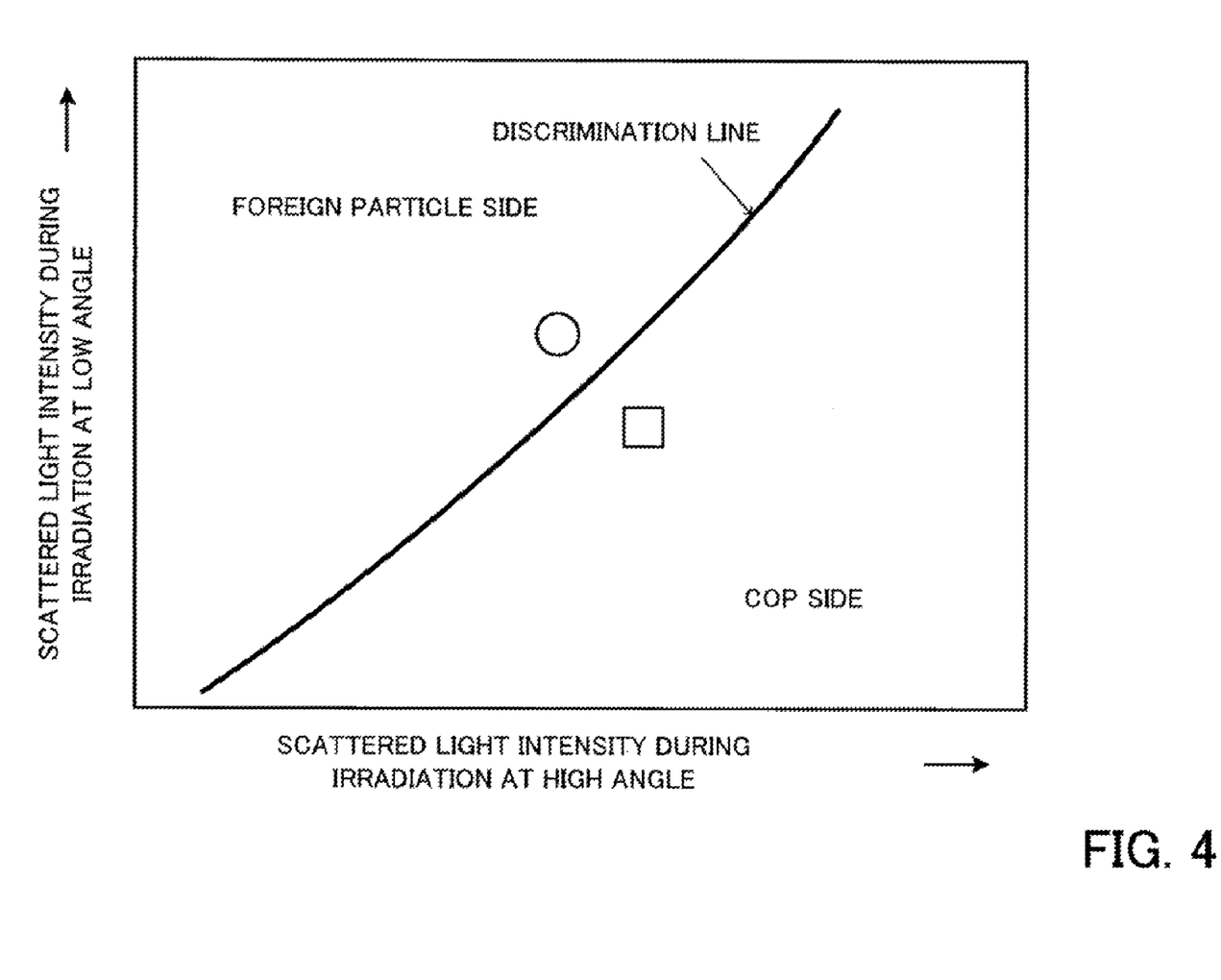
FIG. 4 illustrates a method of discriminating defects using a discrimination line.

Here, FIG. 4 illustrates a method of discriminating defects using the discrimination line. In FIG. 4, the reference discrimination line and the approximation line are not shown.

In step S6, when discriminating the defects detected on the product wafer into foreign particles and COPs, the defects are discriminated into foreign particles and COPs based on whether the scattered light intensities obtained from the defects on the product wafer are in the region above or below the discrimination line. In short, the defect (indicated by a mark ○ in FIG. 4) whose scattered light intensity is in the region above the discrimination line is determined to be a foreign particle, and the defect (indicated by a mark ☐ in FIG. 4) whose scattered light intensity is in the region below the discrimination line is determined to be a COP, as shown in FIG. 4.

After thus discriminating the defects into foreign particles and COPs, only inspection data on the foreign particles is selected based on the discrimination results and sent to an evaluation equipment, for example, a review SEM. Then, the foreign particles on the product wafer are reviewed by SEM to perform a detailed evaluation of the foreign particles (step S7).

Thus, in the review SEM, influences of COPs due to the wafer are eliminated. Therefore, a foreign particle caused by some external factors in the manufacturing process or a region of the foreign particle can be reviewed, so that information on foreign particles can be efficiently obtained.

Accordingly, it becomes possible to analyze review results, to investigate causes of foreign particles, and to take appropriate measures against the manufacturing process causing foreign particles. The appropriate measures include, for example, manufacturing equipment maintenance such as component replacement and cleaning, and modification of manufacturing conditions.

Further, in this inspection, the discrimination line is set. Therefore, the following advantages can be obtained. That is, it is only necessary to perform SEM evaluation only on specific defects selected out of all the detected defects using the reference discrimination line and the approximation line. Accordingly, it is unnecessary to perform SEM evaluation on more defects or all defects.

In addition, it is possible to directly use the scattered light intensities of the detected defects to easily and accurately discriminate the defects into foreign particles and COPs based on whether the scattered light intensities are in the region above or below the discrimination line. Accordingly, it is also unnecessary to perform the processing of correcting the scattered light intensities of the detected defects in the discrimination.

Next, an inspection system for performing the above-described discrimination line setting and wafer inspection will be described.

Figure 5:
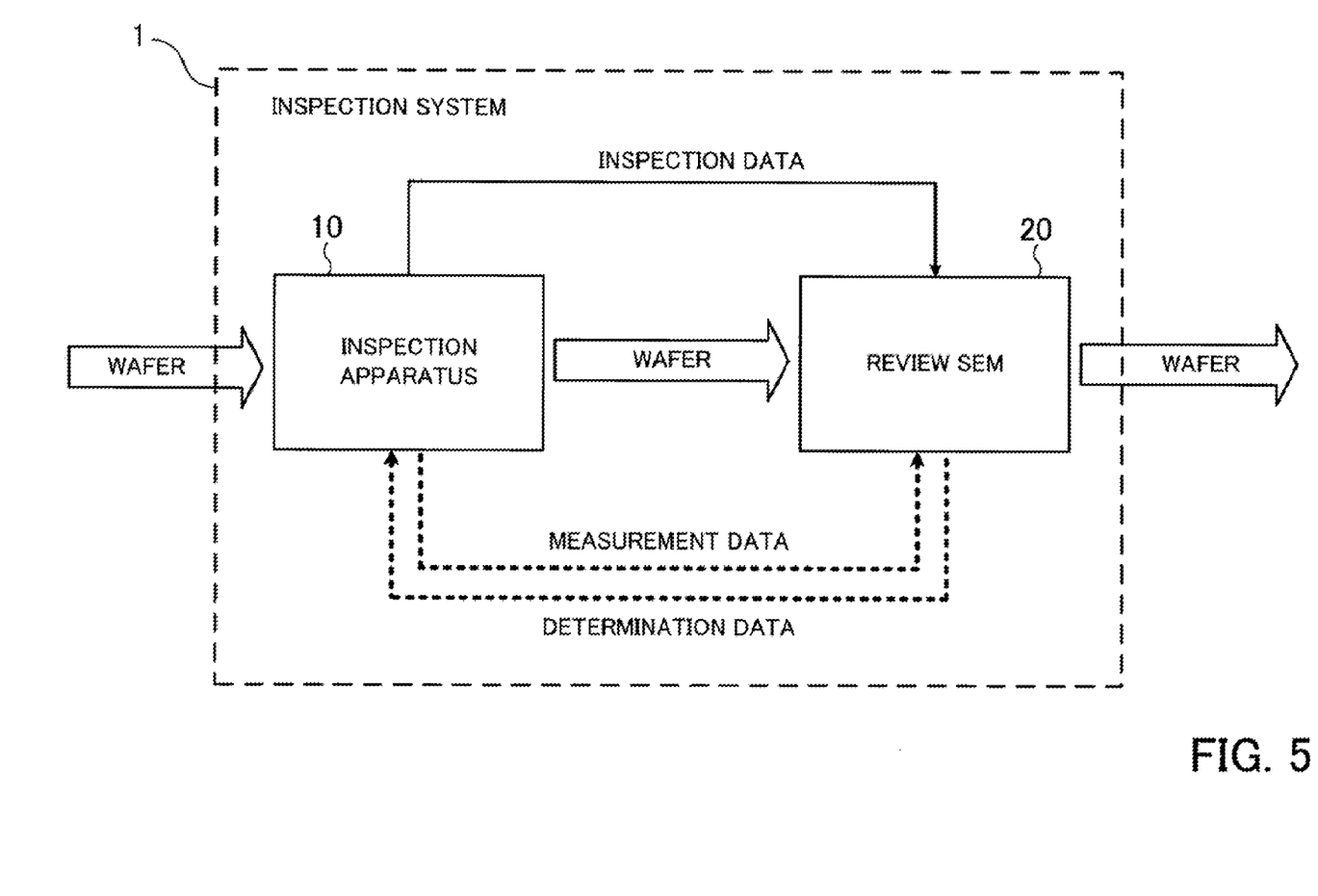
FIG. 5 is a schematic diagram of one example of an inspection system.

FIG. 5 is a schematic diagram of one example of the inspection system.

An inspection system 1 shown in FIG. 5 has an inspection apparatus 10 and a review SEM 20. To the inspection apparatus 10, a wafer (product wafer) processed by a predetermined manufacturing equipment and a wafer (test wafer) for performing a predetermined test are conveyed. In the wafer conveyed to the inspection apparatus 10, the presence or absence, number, density, shape, size and coordinates of defects are inspected by the laser scattering measurement using irradiation with a laser beam at a low angle and at a high angle.

The inspection apparatus 10 has a function of discriminating detected defects into foreign particles and COPs.

Data (inspection data) including the coordinates of the discriminated foreign particles is transmitted to the review SEM 20 using an appropriate wire or wireless communication line. Further, a wafer inspected by the inspection apparatus 10 is conveyed to the review SEM 20.

Using the foreign particle inspection data transmitted from the inspection apparatus 10, the review SEM 20 reviews the foreign particles by SEM. Thus, in the review SEM 20, influences of COPs are eliminated, so that information on foreign particles can be efficiently obtained. Accordingly, it becomes possible to analyze review results, to investigate causes of foreign particles, and to take appropriate measures against the manufacturing process causing foreign particles.

After the review by the review SEM 20, the wafer is conveyed, for example, to a manufacturing equipment of a next process when being a product wafer. When being a test wafer, the wafer is, for example, studied based on the inspection results or conveyed to another test equipment.

Further, this inspection apparatus 10 has a function of setting the discrimination line for discriminating the defects into foreign particles and COPs as described above. To set the discrimination line, defects on predetermined wafers (the above-described standard particle-adhering wafer and foreign particle-adhering wafer) are previously detected by the laser scattering measurement using irradiation with a laser beam at a low angle and at a high angle.

The inspection apparatus 10 transmits to the review SEM 20 specific measurement data (measurement data between the reference discrimination line and the approximation line) as well as defect inspection data corresponding to the measurement data extracted out of the inspection data and the scattered light intensities (measurement data) during the irradiation of laser beam at a low angle and at a high angle, which are obtained in detecting defects on the predetermined wafers.

The review SEM 20 receiving such measurement data automatically determines by SEM measurement whether the defect is a foreign particle or a COP. Then, the review SEM 20 creates data (determination data) indicating the determination results and transmits the determination data to the inspection apparatus 10.

Thereafter, using the received determination data, the inspection apparatus 10 sets the discrimination line on a boundary between the foreign particles and COPs as the determined defects.

Using the thus set discrimination line, the inspection apparatus 10 discriminates the defects detected on the wafer to be reviewed (e.g., product wafer) into foreign particles and COPs as described above. Then, the apparatus 10 transmits only the foreign particle inspection data to the review SEM 20. Thereafter, the review SEM 20 performs a review of the wafer using the foreign particle inspection data.

Subsequently, configurations of the inspection apparatus 10 and the review SEM 20 constituting the inspection system 1 will be described in detail.

Figure 6:
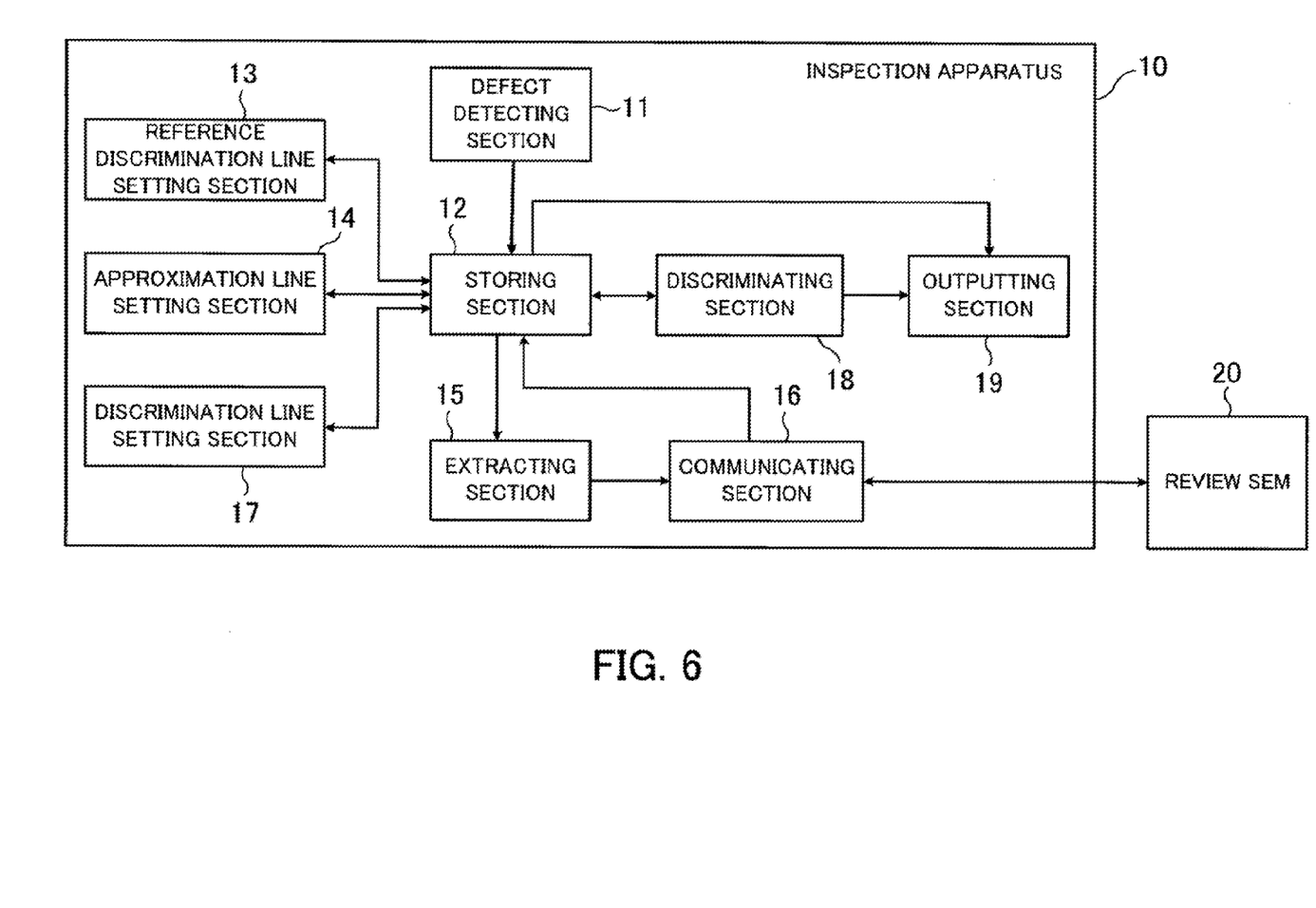
FIG. 6 shows a configuration example of an inspection apparatus.

FIG. 6 shows a configuration example of the inspection apparatus.

As shown in FIG. 6, the inspection apparatus 10 has a defect detecting section 11, a storing section 12, a reference discrimination line setting section 13, an approximation line setting section 14, an extracting section 15, a communicating section 16, a discrimination line setting section 17, a discriminating section 18 and an outputting section 19.

The defect detecting section 11 performs the laser scattering measurement using irradiation with a laser beam at a low angle and at a high angle onto each wafer of the standard particle-adhering wafer, the foreign particle-adhering wafer and the product wafer, thereby detecting the defects on the wafer. In order to perform such defect detection, the section 11 has a mechanism of conveying a wafer and performing alignment to place the wafer. Further, the section 11 has a mechanism of irradiating the placed wafer with a laser beam at a low angle and at a high angle, and a mechanism of detecting scattered light generated by such irradiation of laser beam.

By this defect detecting section 11, coordinates of standard particles, foreign particles and COPs on the wafer are obtained as inspection data as well as scattered light intensities of standard particles, foreign particles and COPs on the wafer, which are measured during irradiation of laser beam at a low angle and at a high angle, are obtained as measurement data.

The storing section 12 stores the inspection data and measurement data on each wafer obtained by the defect detecting section 11. Further, the storing section 12 stores each data on the reference discrimination line and approximation line set using the measurement data, determination data transmitted from the review SEM 20, data on the discrimination line set using the determination data and discrimination data indicating the defect discrimination results obtained using the discrimination line.

The reference discrimination line setting section 13 sets the reference discrimination line using the standard particle measurement data obtained from the standard particle-adhering wafer and stored by the storing section 12. Data on the reference discrimination line set by the setting section 13 is stored by the storing section 12.

The approximation line setting section 14 sets the approximation line using the defect (foreign particle and COP) measurement data obtained from the foreign particle-adhering wafer and stored by the storing section 12. Data on the approximation line set by the approximation line setting section 14 is stored by the storing section 12.

The setting of the reference discrimination line by the reference discrimination line setting section 13 and the setting of the approximation line by the approximation line setting section 14 are performed in accordance with the above-described principles.

The extracting section 15 extracts specific measurement data selected, using the reference discrimination line and the approximation line, out of the measurement data obtained from the foreign particle-adhering wafer and stored by the storing section 12 as well as extracts the defect inspection data corresponding to the measurement data. Further, the extracting section 15 extracts, out of the product wafer inspection data stored by the storing section 12, the inspection data on foreign particles to be reviewed by the review SEM 20.

The communicating section 16 transmits to the review SEM 20 the measurement data and inspection data extracted by the extracting section 15. Further, the communicating section 16 receives the determination data which is transmitted from the review SEM 20 when transmitting the measurement data to the review SEM 20 and which indicates whether the measurement data is of foreign particles or of COPs. The determination data received by the communicating section 16 from the review SEM 20 is stored by the storing section 12.

The discrimination line setting section 17 sets the discrimination line for discriminating the defects into foreign particles and COPs, using the determination data created by the review SEM 20 and stored by the storing section 12. The setting of the discrimination line is performed as follows. In accordance with the above-described principles, the measurement data is discriminated into that of foreign particles and that of COPs based on the determination data received from the review SEM 20 to set the discrimination line on a boundary between the foreign particles and the COPS. The data on the discrimination line set by the discrimination line setting section 17 is stored by the storing section 12.

Using the product wafer measurement data obtained by the defect detecting section 11 and stored by the storing section 12, the discriminating section 18 compares the measurement data with the discrimination line set by the discrimination line setting section 17. Then, the section 18 discriminates based on the comparison whether the defects detected on the product wafer are foreign particles or COPs, thereby creating the data (discrimination data) indicating the discrimination results. The discrimination data created by the discriminating section 18 is stored by the storing section 12. Using the discrimination data, the extracting section 15 extracts the inspection data on foreign particles on the product wafer to be reviewed by the review SEM 20.

The outputting section 19 outputs the discrimination data created by the discriminating section 18 to a display unit or a printer, for example, in the form of a map indicating the respective presence positions of foreign particles and COPs on the product wafer. Further, the section 19 subjects various data stored by the storing section 12 to appropriate processing such as processing of graphing the data in an appropriate form depending on their types. Then, the section 19 outputs the processed data to a display unit or a printer.

Figure 7:
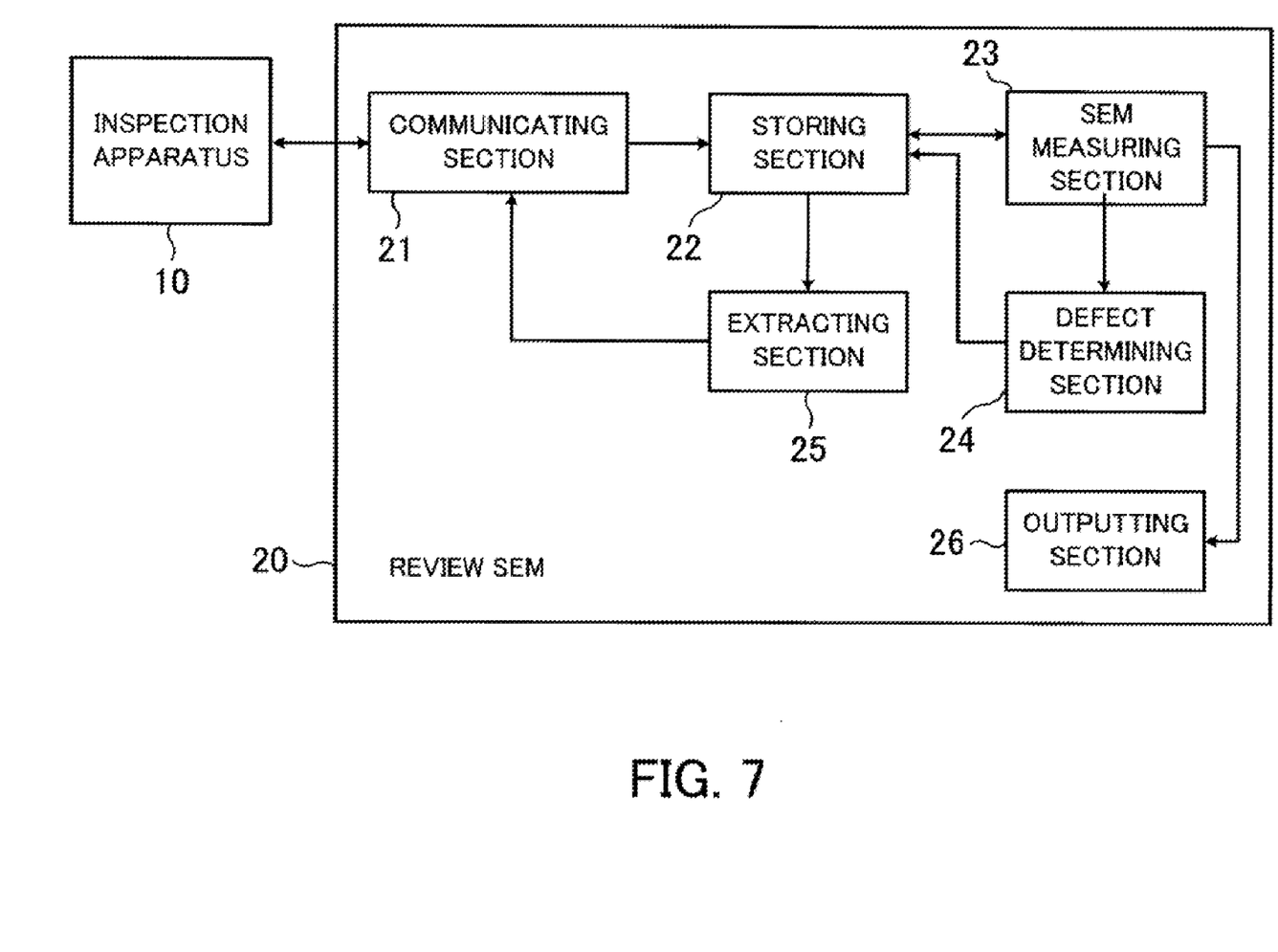
FIG. 7 shows a configuration example of a review SEM.

FIG. 7 shows a configuration example of the review SEM.

As shown in FIG. 7, the review SEM 20 has a communicating section 21, a storing section 22, an SEM measuring section 23, a defect determining section 24, an extracting section 25 and an outputting section 26.

The communicating section 21 receives from the inspection apparatus 10 the specific measurement data and the inspection data corresponding to the measurement data as well as the inspection data on foreign particles discriminated by the inspection apparatus 10. Further, the communicating section 21 transmits to the inspection apparatus 10 the determination data created based on the specific measurement data and inspection data.

The storing section 22 stores the specific measurement data and the inspection data corresponding to the measurement data as well as the inspection data on foreign particles discriminated by the inspection apparatus 10, which are received by the communicating section 21. Further, the section 22 stores the SEM data obtained by SEM measurement and the determination data created using the SEM data.

Using the measurement data and inspection data transmitted from the inspection apparatus 10 and stored by the storing section 22, the SEM measuring section 23 measures the corresponding defect by SEM, thereby creating the SEM data indicating the measurement results. The created SEM data is stored by the storing section 22.

Using the SEM data created by the SEM measuring section 23, the defect determining section 24 determines whether the defects are foreign particles or COPs, thereby creating the determination data indicating the determination results. The created determination data is stored by the storing section 22.

The extracting section 25 extracts the determination data stored by the storing section 22. The extracted determination data is transmitted to the inspection apparatus 10 by the communicating section 21.

The outputting section 26 subjects the SEM data created by the SEM measuring section 23 to appropriate processing, and outputs the processed SEM data to a display unit or a printer.

Subsequently, a processing flow of the inspection system 1 having the above-described configuration will be described in detail.

First, a processing flow of the inspection apparatus 10 will be described.

Here, description will be made on a case of first setting the discrimination line, discriminating the defects on the product wafer using the discrimination line, and reviewing the foreign particles on the product wafer.

Figure 8:
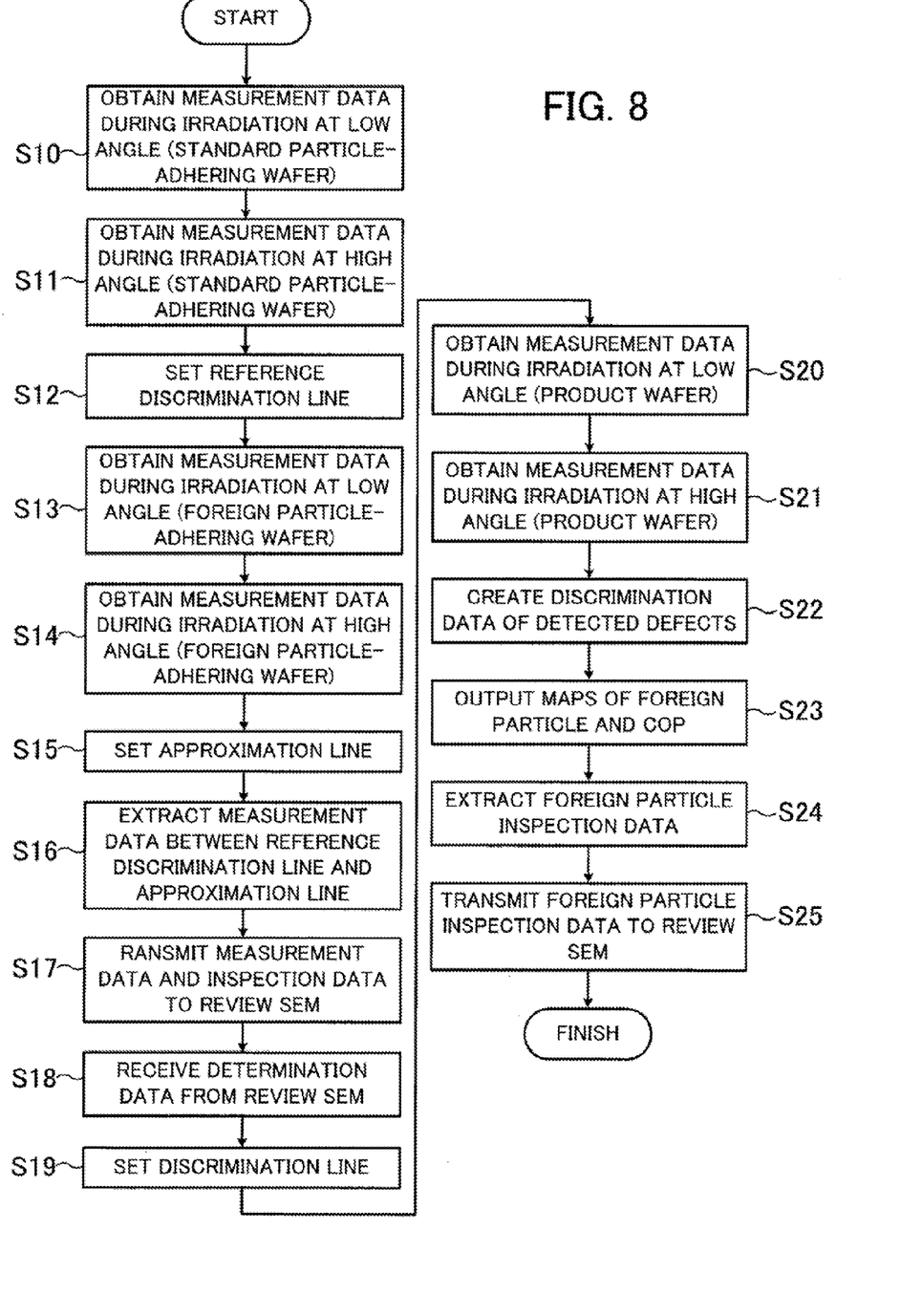
FIG. 8 shows one example of a processing flow of an inspection apparatus.

FIG. 8 shows one example of a processing flow of the inspection apparatus.

In the inspection apparatus 10, defect detection processing on the standard particle-adhering wafer by the laser scattering measurement is first performed to set the discrimination line.

During the processing, the defect detecting section 11 measures the scattered light intensities by irradiating the standard particle-adhering wafer with a laser beam at a low angle to obtain the measurement data during irradiation of laser beam at a low angle (step S10). Subsequently, the defect detecting section 11 measures the scattered light intensities by irradiating the standard particle-adhering wafer with a laser beam at a high angle to obtain the measurement data during irradiation of laser beam at a high angle (step S1). The measurement data obtained from the standard particle-adhering wafer is stored by the storing section 12.

During this defect detection processing, the measurement data during irradiation of laser beam at a low angle may be obtained after obtaining the measurement data during irradiation of laser beam at a high angle.

After the defect detection processing on the standard particle-adhering wafer, the reference discrimination line setting section 13 sets the reference discrimination line using the measurement data obtained from the standard particle-adhering wafer (step S12). The obtained data on the reference discrimination line is stored by the storing section 12.

Next, in the inspection apparatus 10, defect detection processing on the foreign particle-adhering wafer by the laser scattering measurement is similarly performed to set the discrimination line.

During the processing, the defect detecting section 11 obtains the measurement data during irradiation of laser beam onto the foreign particle-adhering wafer at a low angle (step S13). Subsequently, the defect detecting section 11 obtains the measurement data during irradiation of laser beam onto the foreign particle-adhering wafer at a high angle (step S14). The measurement data obtained from the foreign particle-adhering wafer is stored by the storing section 12.

During this defect detection processing, the measurement data during irradiation of laser beam at a low angle may be obtained after obtaining the measurement data during irradiation of laser beam at a high angle.

Further, the foreign particle-adhering wafer is conveyed to the review SEM 20, for example, at the stage where the defect detection processing in steps S13 and S14 is completed.

After the defect detection processing on the foreign particle-adhering wafer, the approximation line setting section 14 sets the approximation line using the measurement data obtained from the foreign particle-adhering wafer (step S15). The obtained data on the approximation line is stored by the storing section 12.

Next, using each data on the reference discrimination line and the approximation line, the extracting section 15 extracts from the storing section 12 the measurement data between the reference discrimination line and the approximation line as well as the defect inspection data corresponding to the measurement data out of all the measurement data and inspection data obtained from the foreign particle-adhering wafer (step S16).

Next, the communicating section 16 transmits to the review SEM 20 the extracted measurement data and inspection data on the foreign particle-adhering wafer (step S17). Further, the communicating section 16 receives from the review SEM 20 the defect determination data corresponding to the transmit data (step S18). The received determination data is stored by the storing section 12.

Next, the discrimination line setting section 17 sets the discrimination line using the determination data created by the review SEM 20 (step S19). The obtained data on the discrimination line is stored by the storing section 12.

After the setting of the discrimination line, the defect detection processing on the product wafer by the laser scattering measurement is performed in the inspection apparatus 10.

During the processing, the defect detecting section 11 obtains the measurement data during irradiation of laser beam onto the product wafer at a low angle (step S20). Subsequently, the defect detecting section 11 obtains the measurement data during irradiation of laser beam onto the product wafer at a high angle (step S21). The measurement data obtained from the product wafer is stored by the storing section 12.

During this defect detection processing, the measurement data during irradiation of laser beam at a low angle may be obtained after obtaining the measurement data during irradiation of laser beam at a high angle.

Further, the product wafer is conveyed to the review SEM 20, for example, at the stage where the defect detection processing in steps S20 and S21 is completed.

Further, the discriminating section 18 compares the measurement data on the product wafer with the previously set discrimination line. Then, the section 18 discriminates defects detected on the product wafer into foreign particles and COPs, thereby creating discrimination data (step S22). The created discrimination data is stored by the storing section 12.

Next, using the discrimination data, the outputting section 19 outputs a map indicating the respective presence positions of foreign particles and COPs on the product wafer (step S23).

Figure 9:
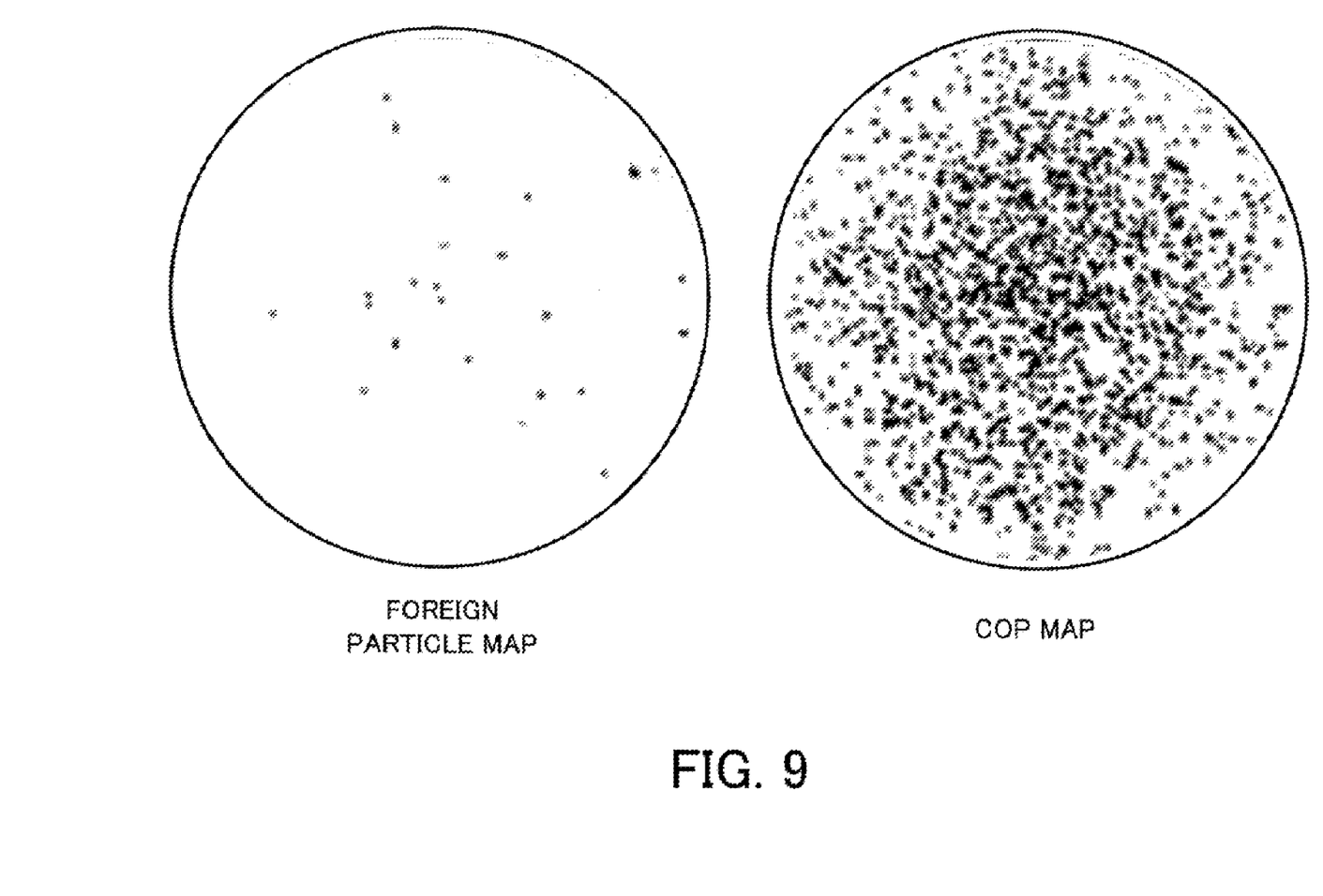
FIG. 9 shows one example of a map.

Here, FIG. 9 shows one example of the map. The inspection apparatus 10 first discriminates the defects detected on the product wafer into foreign particles and COPs. Then, using the discrimination data, the inspection apparatus 10 outputs each of the map (foreign particle map) indicating presence positions of foreign particles and the map (COP map) indicating presence positions of COPs on the product wafer, as shown in FIG. 9.

The output of maps as in step S23 may be performed, if desired.

The flow returns to FIG. 8. After the creation of the discrimination data on the product wafer, the extracting section 15 extracts, using the discrimination data, only the foreign particle inspection data out of the defect inspection data on the product wafer stored by the storing section 12 (step S24). Then, the communicating section 16 transmits to the review SEM 20 the extracted foreign particle inspection data on the product wafer (step S25).

Figure 10:
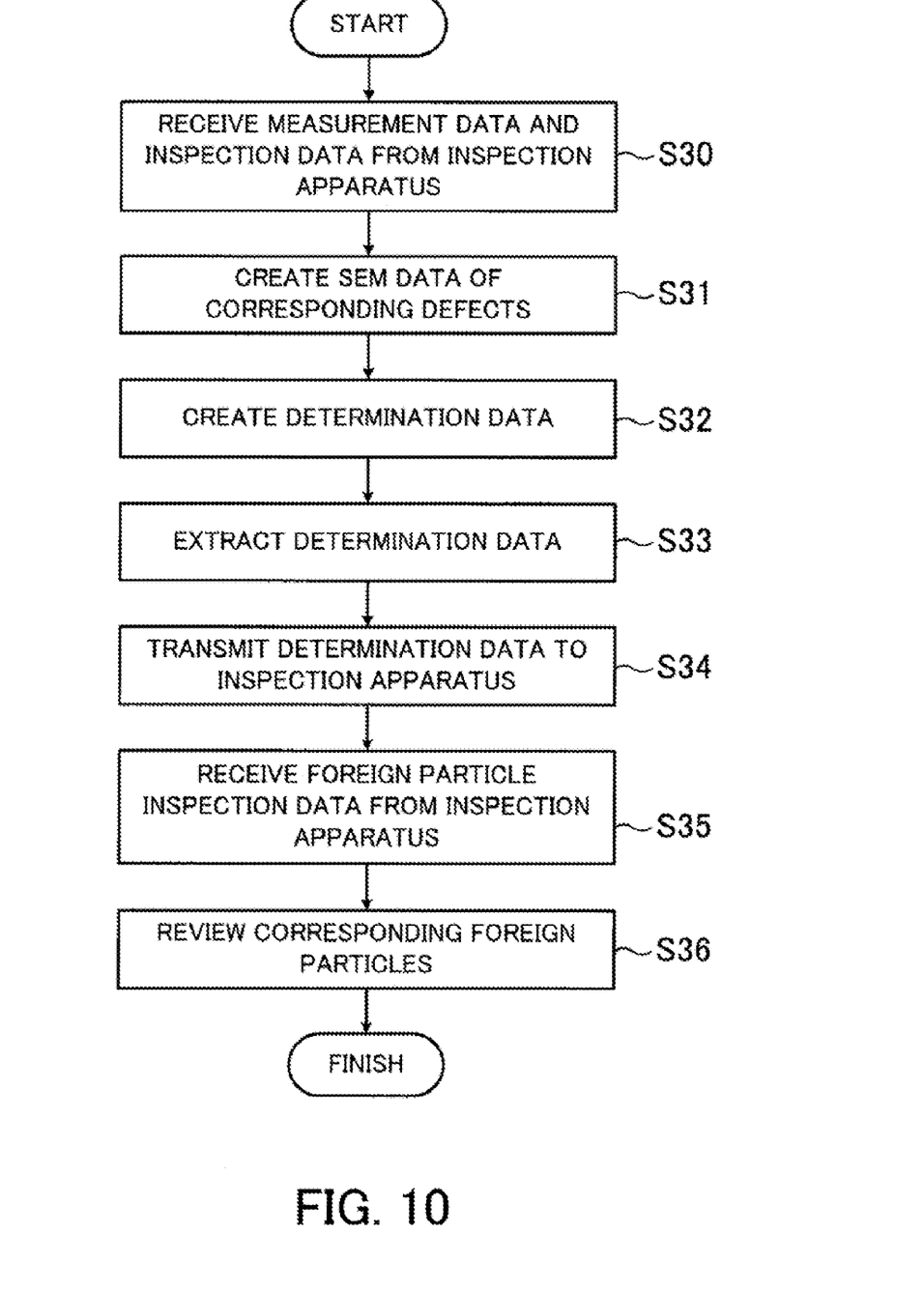
FIG. 10 shows one example of a processing flow of a review SEM.

FIG. 10 shows one example of a processing flow of the review SEM.

First, the foreign particle-adhering wafer after the defect detection processing is conveyed from the inspection apparatus 10 to the review SEM 20.

The communicating section 21 receives the measurement data and inspection data transmitted from the inspection apparatus 10 in step S17 of FIG. 8 (step S30). The received measurement data and inspection data are stored by the storing section 22.

Next, using the measurement data and inspection data transmitted from the inspection apparatus 10, the SEM measuring section 23 performs an SEM measurement on the corresponding defects on the foreign particle-adhering wafer, thereby creating the SEM data (step S31). The created SEM data is outputted by the outputting section 26 in the form of screen images corresponding to the contents.

Then, using the created SEM data, the defect determining section 24 determines whether the defects measured by SEM are foreign particles or COPs, thereby creating the determination data (step S32). The created determination data is stored by the storing section 22.

The extracting section 25 extracts the determination data from the storing section 22 (step S33). Then, the communicating section 21 transmits the determination data to the inspection apparatus 10 (step S34).

After the defect determination processing on the foreign particle-adhering wafer, the product wafer after the defect detection processing is conveyed from the inspection apparatus 10 to the review SEM 20.

The communicating section 21 receives the foreign particle inspection data on the product wafer from the inspection apparatus 10 in step S25 of FIG. 8 (step S35). The received foreign particle inspection data is stored by the storing section 22.

Then, using the foreign particle inspection data, the SEM measuring section 23 reviews the corresponding foreign particles on the product wafer (step S36). Data indicating the review results is stored by the storing section 22, and outputted by the outputting section 26 in the form of screen images corresponding to the contents.

Thus, in the inspection system 1, the reference discrimination line is set using standard particles, the approximation line is set using foreign particles, and the discrimination line used for the discrimination between foreign particles and COPs is set using these reference discrimination line and the approximation line. By using the thus set discrimination line, defects can be easily and highly accurately discriminated into foreign particles and COPs. Further, in the review SEM 20, influences of COPs due to the wafer are eliminated, so that information on foreign particles can be accurately and effectively obtained. Accordingly, it becomes possible to perform more appropriate analysis and to take more appropriate measures based on the analysis. As a result, it becomes possible to attain improvement in a quality of semiconductor devices as well as to attain improvement in a yield during manufacture.

The processing flow of the inspection system 1 is here described by taking as an example a case of discriminating the defects on the product wafer using the discrimination line to review foreign particles; however, the wafer used here is not necessarily a product wafer and may be, for example, a test wafer for investigation whether the manufacturing equipment is normally operated. When performing the above-described evaluation of foreign particles using such a wafer, operation conditions of the manufacturing equipment can be appropriately grasped.

The respective processing functions of the inspection apparatus 10 and the review SEM 20 of the inspection system 1 can be realized using a computer.

In general, a computer includes a CPU (Central Processing Unit), a ROM (Read Only Memory), a RAM (Random Access Memory), an HDD (Hard Disk Drive), a graphics processor, an input interface and a communication interface, and these are connected via a bus. Here, the CPU executes processing described in a program stored in the HDD. The ROM stores fundamental programs or data executed by the CPU.

The RAM stores a program or data in execution by the CPU. The HDD stores OS (Operating System), an application program or various types of data executed by the CPU. The graphics processor causes screen images to be displayed on the display unit in accordance with drawing instructions from the CPU. To the input interface, a mouse and a keyboard are connected, thereby receiving information inputted by users and transmitting the information to the CPU via the bus. The communication interface is an interface for a LAN (Local Area Network) connection among respective computers.

When the above-described respective processing functions of the inspection apparatus 10 and the review SEM 20 are realized by computers, a program containing processing contents of functions to be provided on the inspection apparatus 10 and the review SEM 20 is provided. By executing the program using a computer, the above-described processing functions can be realized on the computer. The program containing the processing contents can be recorded on a computer-readable recording medium. Examples of the computer-readable recording medium include a magnetic recording system such as the HDD, an optical disk such as a DVD (Digital Versatile Disk) and a CD-ROM (Compact Disc Read Only Memory), a magnetooptical medium such as an MO (Magneto-Optical disk) and a semiconductor memory.

In the case of distributing a program, portable recording media such as a DVD and CD-ROM having recorded thereon the program are sold. Further, a program may be stored in a storage device of a server computer so as to be transferred from the server computer to another computer through the network. A computer which executes programs stores in its own storage device, for example, a program recorded on a portable recording medium or a program transferred from a server computer. Then, the computer reads a program from its own storage device and executes processing according to the program. The computer can also directly read a program from a portable recording medium and execute processing according to the program.

The above description is made by taking as an example a case of discriminating the defects detected on the wafer into foreign particles and COPs. In addition to wafers, the present invention can be similarly applied also to a tabular object to be inspected such as an ALTIC substrate, a glass substrate and a disk substrate. A combination of defects is not limited to that of foreign particles and COPs. The present invention can be similarly applied also to another combination such as a combination of foreign particles and scratches. Further, the number of types of the defects to be treated is not limited to two types. Even when three types or more of defects are treated, these defects can be similarly discriminated.

In the present invention, the inspection method is designed to comprise the steps of: irradiating predetermined particles and plural types of defects with a laser beam to measure scattered light intensities; determining types of some defects selected out of the plural types of defects using the measured scattered light intensities; setting a discrimination line based on the determination; and discriminating, using the discrimination line, the defects on an object to be inspected.

Therefore, the defects on the object to be inspected can be easily and highly accurately discriminated depending on their types. As a result, information on specific types of defects selected out of the defects on the object to be inspected can be accurately and effectively obtained. Accordingly, appropriate measures can be taken based on the information, so that it becomes possible to attain improvement in a quality of semiconductor devices as well as to attain improvement in a yield during manufacture.

The foregoing is considered as illustrative only of the principles of the present invention. Further, since numerous modifications and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. A method of inspecting defects on an object comprising:
   irradiating predetermined particles with a laser beam to measure first scattered light intensities;
   irradiating plural types of defects with the laser beam to measure second scattered light intensities;
   determining types of some defects selected out of the plural types of defects using the first scattered light intensities;
   setting, based on the determination, a discrimination line indicating a boundary value of the second scattered light intensities, the boundary value being in dependence on the types; and
   discriminating, using the discrimination line, defects on the object.

2. The method according to claim 1, wherein:
   in determining types of some defects,
   a reference discrimination line indicating a boundary value of the first scattered light intensities is set;
   an approximation line of the second scattered light intensities defects is set; and
   the types of the some defects between the reference discrimination line and the approximation line are determined.

3. The method according to claim 1, wherein the some defects are evaluated by SEM to determine the types.

4. The method according to claim 1, wherein:
   in irradiating the predetermined particles with the laser beam, the predetermined particles are irradiated with the laser beam at first and second angles respectively; and
   in irradiating the plural types of defects with the laser beam, the plural types of defects are irradiated with the laser beam at the first and second angles respectively.

5. The method according to claim 1, wherein:
   in discriminating, the object is irradiated with the laser beam to measure third scattered light intensities;
   the third scattered light intensities are compared with the discrimination line; and
   the defects on the object are discriminated based on the comparison.

6. The method according to claim 1, wherein after discriminating the defects on the object, specific defects discriminated out of the defects on the object are evaluated.

7. An inspection system of inspecting defects on an object comprising:
   a storing section storing first scattered light intensities based on predetermined particles and second scattered light intensities based on plural types of defects;
   a determining section determining types of some defects selected out of the plural types of defects using the first scattered light intensities;
   a first setting unit for setting, based on the determination, a discrimination line indicating a boundary value of the second scattered light intensities, the boundary value being in dependence on the types; and
   a discriminating section discriminating, using the set discrimination line, defects on the object.

8. The inspection system according to claim 7, further comprising:
   a second setting section setting a reference discrimination line indicating a boundary value of the first scattered light intensities; and
   a third setting section setting an approximation line of the second scattered light intensities, wherein:
   the determining section determines the types of the some defects between the set reference discrimination line and approximation line.

9. The inspection system according to claim 7, wherein the determining section evaluates the some defects by SEM to determine the types.

10. The inspection system according to claim 7, wherein:
    the storing section stores the first scattered light intensities based on the predetermined particles with a laser beam at first and second angles respectively, and
    stores the second scattered light intensities based on the plural types of defects with the laser beam at the first and second angles respectively.

11. The inspection system according to claim 7, wherein the discriminating section compares the scattered light intensities measured from the defects on the object with the discrimination line and discriminates, based on the comparison, the defects on the object.

12. The inspection system according to claim 7, further comprising review section evaluating specific defects discriminated out of the defects on the object.

13. An inspection apparatus used for inspecting defects on an object comprising:
    a storing section storing a first scattered light intensities based on predetermined particles and second scattered light intensities based on plural types of defects;
    an extracting section extracting some defects selected out of the plural types of defects using the second scattered light intensities;
    a determining section determining types of the some defects using the first scattered light intensities;
    a first setting section setting, using a data indicating determination results, a discrimination line indicating a boundary value of the second scattered light intensities, the boundary value being in dependence on the types; and
    discriminating section discriminating, using the discrimination line, defects on the object.

14. The inspection apparatus according to claim 13, further comprising:
- a second setting section setting a reference discrimination line indicating a boundary value of the first scattered light intensities; and
- a third setting section setting an approximation line of the second scattered light intensities, wherein:
- the extracting section extracts the some defects between the reference discrimination line and approximation line.

15. The inspection apparatus according to claim 13, wherein:
- the storing section stores the first scattered light intensities based on the predetermined particles with a laser beam at first and second angles respectively, and stores the second scattered light intensities based on the plural types of defects with a laser beam at the first and second angles respectively.

16. The inspection apparatus according to claim 13, wherein the discriminating section compares the scattered light intensities measured from the defects on the object with the discrimination line and discriminates, based on the comparison, the defects on the object.

17. The inspection apparatus according to claim 13, further comprising a communicating section transmitting, to an evaluation apparatus, data on specific defects discriminated out of the defects on the object.

18. The inspection apparatus according to claim 13, wherein the evaluation apparatus is a review SEM.

* * * * *